United States Patent
Matsutani et al.

(10) Patent No.: US 6,524,104 B2
(45) Date of Patent: *Feb. 25, 2003

(54) DENTAL INSTRUMENT FOR ROOT CANAL THERAPY

(75) Inventors: Kanji Matsutani, Tochigi-ken (JP); Hideyuki Murai, Tochigi-ken (JP); Toshiyuki Takase, Tochigi-ken (JP)

(73) Assignee: Mani, Inc., Tochigi-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 16 days.

(21) Appl. No.: 09/736,269

(22) Filed: Dec. 15, 2000

(65) Prior Publication Data

US 2001/0034005 A1 Oct. 25, 2001

(30) Foreign Application Priority Data

Dec. 16, 1999 (JP) .......................... 11-357927

(51) Int. Cl.$^7$ ................................................ A61C 5/02
(52) U.S. Cl. ................................................ 433/102
(58) Field of Search ................................. 433/102, 224

(56) References Cited

U.S. PATENT DOCUMENTS

| 4,934,934 | A | * | 6/1990 | Arpaio, Jr. et al. ......... 433/102 |
| 5,464,362 | A | * | 11/1995 | Heath et al. ............. 433/102 X |
| 5,762,497 | A | * | 6/1998 | Heath ......................... 433/102 |

* cited by examiner

Primary Examiner—Nicholas D. Lucchesi
(74) Attorney, Agent, or Firm—Townsend & Banta

(57) ABSTRACT

A dental instrument for root canal therapy having a shaft portion and an operational portion extended from such shaft portion, wherein at least a region from the tip of the operational portion down to a predetermined distant position has a sectional form surrounded by an arc and a chord, and a length of a line segment along a vertical bisector of the chord sectioned between such chord and such arc equals to or longer than five-eighths of the diameter of a virtual circle composed by such arc was disclosed.

7 Claims, 5 Drawing Sheets

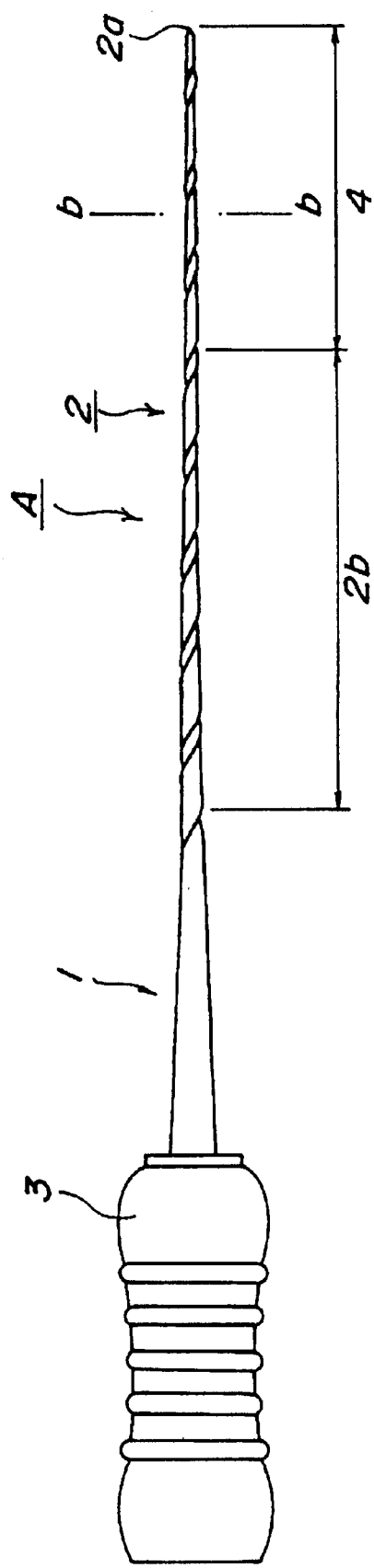
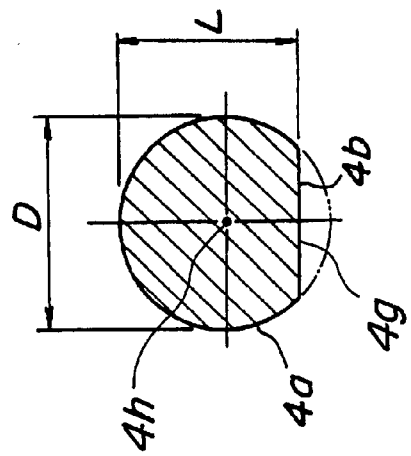

Graph of experimental result of various piercing instrument

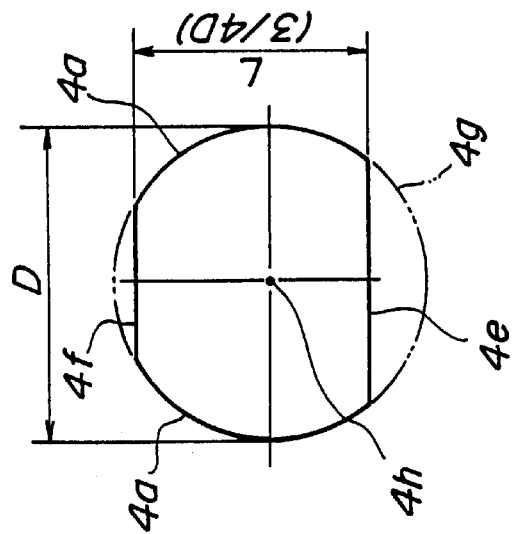
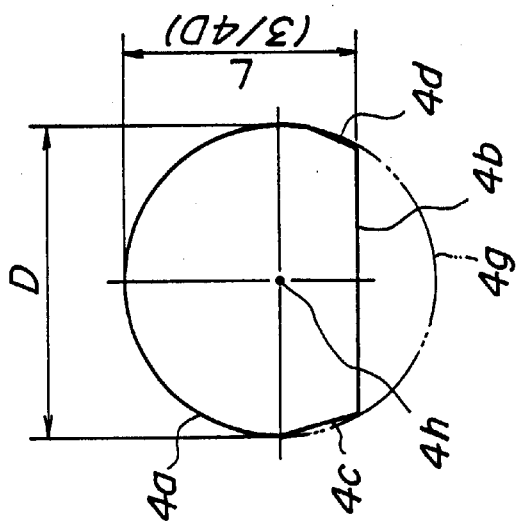
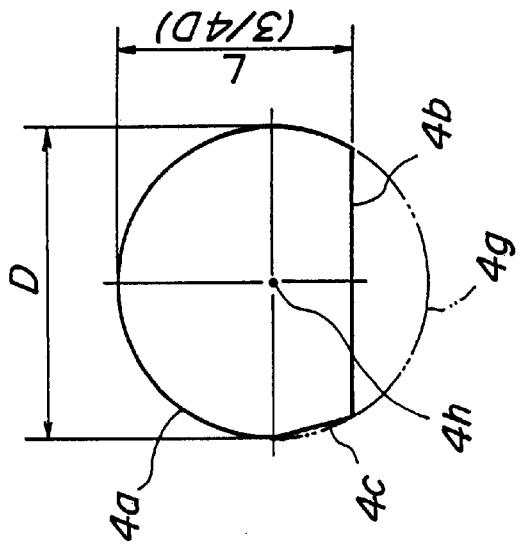

FIG.4 rootcanal insert resistration comparative test

| cross-section shape | insert resistration (gcm) | | | | cross-section area ratio |
|---|---|---|---|---|---|
| | 1 | 2 | average | standerd deviation | |
| 50%section(semicircle) | 159.4 | 137.6 | 148.5 | 15.4 | 0.50 |
| 62.5%section(5/8circle) | 191.3 | 220.1 | 205.7 | 20.4 | 0.67 |
| 75%section(3/4circle) | 232.4 | 244.8 | 238.6 | 8.8 | 0.85 |
| 87.5%section(7/8circle) | 272.4 | 285.3 | 278.9 | 9.1 | 0.95 |
| 93.8%section(15/16circle) | 306.1 | 292.6 | 299.4 | 9.5 | 0.99 |
| 100%section(circle) | 308.3 | 332.7 | 320.5 | 17.3 | 1.00 |
| K-FILE#10 | 193.6 | 241.6 | 204.1 | 14.8 | 0.64 |

FIG.5 bending comparative test

| cross-section shape | 1 | 2 | 3 | bending average | torque(gcm) standerd deviation |
|---|---|---|---|---|---|
| 50%section(semicircle) | 7 | 6 | 7 | 6.7 | 0.6 |
| 62.5%section(5/8circle) | 10 | 11 | 11 | 10.7 | 0.6 |
| 75%section(3/4circle) | 13 | 13 | 14 | 13.3 | 0.6 |
| 87.5%section(7/8circle) | 14 | 16 | 16 | 15.3 | 1.2 |
| 93.8%section(15/16circle) | 15 | 16 | 16 | 15.7 | 0.6 |
| 100%section(circle) | 16 | 16 | 16 | 16.0 | 0.0 |
| K-FILE#10 | 8 | 9 | 9 | 8.7 | 0.6 |

DENTAL INSTRUMENT FOR ROOT CANAL THERAPY

TECHNICAL FIELD

The present invention relates to a dental instrument for root canal therapy, and in particular to a dental instrument for piercing content filled in a root canal at the beginning of root canal therapy, and resecting if necessary a hard projection which appears on the root canal, to thereby make a route for allowing access of other dental instruments for root canal therapy.

BACKGROUND ART

In root canal therapy in dentistry, it is a common practice to resect a calcified root canal wall extending towards an apical portion and to remove resection debris and contents of the root canal to thereby expose a new surface of the root canal. In such therapy, dentists generally choose an instrument for root canal therapy most applicable to the target therapy from their suite of instruments categorized by sizes such as a reamer, K-file and H-file, and handle such instrument directly by a hand or indirectly as being attached to a hand piece, where advancement of the therapy is sensible through the operation of the instrument.

The reamer is composed of a triangle-sectioned or square-sectioned rod material twisted at a small angle, and mainly functions when being operated in a rotating manner so as to resect the root canal wall and remove resection debris and contents of the root canal. The K-file is composed of a triangle-sectioned or square-sectioned rod material twisted at a relatively large angle, and mainly functions when being operated in a reciprocal manner so as to resect the root canal wall and remove resection debris and contents of the root canal. The H-file is composed of a rod material shaped so as to have a sectional form surrounded by a part of straight line in the radial direction and a spiral curve, and mainly functions when being operated in a reciprocal manner so as to resect the root canal wall and remove resection debris and contents of the root canal.

The root canal has a curved and tapered form with the opening thereof shrinks toward the apical portion, where the curved form significantly differs from patient to patient. Thus the instruments for root canal therapy such as the reamer, K-file, H-file and so forth are designed to be highly flexible so as to fit themselves the root canal (root canal wall) which has a tapered and curved form differs with patients.

The instruments for root canal therapy such as the reamer, K-file, H-file and the like are preferably made of austenitic stainless steel which is not causative of fracture or chipping during the therapy and rusting. The applicant of the present invention holds a technology for fabricating various surgical needles and instruments for root canal therapy using austenitic stainless steel which is drawn in a fiber form by cold wire drawing so as to attain an excellent hardness and bending strength.

It is to be noted now that the root canal is filled with the content (dental pulp) including nerve, blood vessel, lymph vessel and so forth, which is sometimes found solidified. Thus the curved profile of the root canal or constricted state of the wall thereof due to calcification is not visible at the start of the therapy. When the therapy is started with an instrument for root canal therapy such as a reamer, K-file, H-file or the like, the tip portion of such instrument pierced into the content within the root canal is applied with a load which is ascribable to resistance during such piercing, and further applied with another load depending on the applied operational force when the tip portion penetrating the content comes into contact with the root canal wall.

Timing on which the tip portion of the instrument for root canal therapy comes into contact with the root canal wall varies depending on conditions such as curved profile of the root canal and the constricted state of the wall thereof due to calcification, so that it is difficult to regulate operation of the instrument for root canal therapy so as to reduce the force applied therethrough upon such contact, and instead the tip portion is applied with a large load upon such contact. The load often exceeds an allowable limit of such instrument for root canal therapy, and raises a problem that the instrument becomes unavailable due to a permanent deformation in the tip portion. Even known is a case in which the tip portion is folded, which is more serious problem surpassing wear of the instrument for root canal therapy.

Of course such therapy must be safety-oriented since the therapy is targeted at the root canal wall invisible due to the filled content. An instrument for root canal therapy larger in size and having a larger allowable load than that of a just-in-size instrument may solve the foregoing problem of the folded tip, but such instrument is more likely to be obstructed by the root canal wall and to fail in creating an access route. On the other hand, using an instrument for root canal therapy smaller in size may result in frequent deformation of the tip portion thereof, which consumes plural sizes of the instruments only in a single therapy.

The foregoing problem can be solved by beginning the therapy with creating an access route, which is helpful for guiding the instrument for root canal therapy, in the content filled within the root canal, and then by selecting a reamer, K-file, H-file or the like which is most suitable for such access route. To ensure such function to be exhibited, it is sufficient for the instrument for root canal therapy to have a strength durable enough against the load which is ascribable to resistance of the content in the root canal or to collision with the root canal wall.

In recent years, there is provided a therapeutic instrument used at the beginning of the therapy for creating an access route in the content filled in the root canal. The therapeutic instrument is made of a hardened carbon steel. Such therapeutic instrument is successful in obtaining larger bending strength as compared with that for an instrument made of austenitic stainless steel, so that it can effectively create in the root canal the access route for guiding other instruments for root canal therapy by reciprocal and rotating operation even when the root canal is filled with contents which is sometimes even solidified.

In the fabrication of such reamer and files, a round rod (wire) is directly ground to produce slant planes according to a desired taper so as to obtain a tapered and edged wire having a square, triangle or rectangular section. In the fabrication of the H-file, a round rod is directly ground with a single stroke.

As described in the above, a conventional problem resides in that the reamer, K-file and H-file are likely to be wasted during the root canal therapy after being excessively bended or permanently deformed due to load ascribable to the content in the root canal or contact with the root canal wall. This may result in use or wasting of excessive suite of the instruments for root canal therapy, and thus may further result in increased time and cost for the therapy. In some cases, such therapeutic instrument even cannot make the access route toward the apical portion.

On the other hand, hardening is indispensable for a therapeutic instrument which overcame the foregoing problem by using carbon steel. The portion to be hardened is, however, very thin and has only a small heat capacity, so that it is not easy to uniformly elevate the temperature of the entire portion of the instrument, and as a result to attain a uniform strength over the entire length of the instrument, which may also result in difficulty in ensuring uniformity of a number of the therapeutic instruments. This can even raise a serious problem that the suite of the instrument accidentally contain a brittle product which may chip within the root canal. Another problem resides in that the instrument made of carbon steel readily gets rust due to the specific nature of this material, and sterilizing such instrument once used in an autoclave may corrode and ruin the instrument. Removing the generated rust may degrade the strength below a desired level. Thus the instrument once used is to be disposed, which pushes up the cost for the instrument.

It is therefore an object of the present invention to provide a dental instrument for root canal therapy really capable of creating at the beginning of the therapy an access route for guiding other instruments for root canal therapy, and a method for fabricating such instrument at a low cost and with a high reliability.

SUMMARY OF THE INVENTION

The present inventors found out after extensive experiments for obtaining a dental instrument for root canal therapy free from the foregoing problems that the following factors are necessary to create in the content of a root canal an access route for guiding a reamer, K-file or H-file.

A first factor is that the tip portion of the instrument should have a bending strength enough to withstand the load generated when the tip portion is thrust into the content, and in particular for the case that the root canal is constricted due to curved profile thereof or calcification, that the tip portion of the instrument should have a bending strength enough to withstand the load generated when the tip portion accidentally comes into contact with the root canal wall at the constricted portion.

Since the instrument can achieve an object only by such thrusting, it is necessary, while considering a bending strength of a similarly operated K-file as a standard, for the instrument of the present invention to have a strength sufficiently larger than that of the K-file.

Selecting a material with a high strength is important for improving the bending strength. A material essentially requires hardening, however, tends to cause hardening-related dispersion; and a material likely to rust does not allow preliminarily sterilization, has difficulty in the repetitive use, and has only a limited duration of the storage. It is thus preferable to use austenitic stainless steel which is not causative of rusting, and it is also preferable that the material is drawn in a fiber form by cold wire drawing so as to attain an excellent hardness and bending strength.

Using a cold-drawn austenitic stainless steel and defining a certain sectional form of the instrument will desirably improve the bending strength.

A second factor is that the content filled in the root canal can readily maigrate. It is not always necessary to remove the content outside the root canal, and only dislocation within the root canal so as to allow creation of the access route can suffice. To dislocate the content within the root canal, it is essential to ensure a certain gap, which allows such content to migrate, between the tip portion of the dental instrument for root canal therapy and the root canal wall.

A third factor is that the resistance caused by the piercing of the instrument into the content of the root canal should be small as possible. It is necessary for the instrument used herein that the surface of the portion pierced into the content should have a less amount of irregularity. In particular when the instrument is pierced into the content, a subtle touch upon contact of the tip portion with the root canal wall or other materials should be sensible by a dentist operating such instrument. Thus while being preferably low, the resistance is also required to have a certain level so that a dentist can sense it.

A fourth factor is that the instrument should have a minimum cutting edge so as to cut a constricted portion of the root canal due to the curved profile or calcification. The instrument, originally designed to create an access route, should be extra thin, where the tip portion of which preferably has a diameter of 0.06 mm to 0.15 mm, and more preferably 0.06 mm to 0.10 mm. Thus the instrument is flexible enough to bend along the curved root canal. It is thus necessary for the instrument to have a rigid cutting edge capable of cutting the solidified content or projections thrust out from the root canal wall.

A dental instrument for root canal therapy according to the present invention which can satisfy the above factors has a shaft portion and an operational portion extended from such shaft portion, wherein at least a region from the tip of the operational portion down to a predetermined distant position has a sectional form surrounded by an arc and a chord, and a length of a line segment along a vertical bisector of the chord sectioned between such chord and such arc equals to or longer than five-eighths of the diameter of a virtual circle composed by such arc.

Using such dental instrument for root canal therapy, an effective access route can be created in the content filled in the root canal at the beginning of root canal therapy. (The dental instrument for root canal therapy of the present invention is hereinafter referred to as "piercing instrument" since the instrument is intrinsically targeted at creating an access route).

Since the piercing instrument has a region from the tip of the operational portion down to a predetermined distant position whose sectional form is surrounded by an arc and a chord, and a length of a line segment along a vertical bisector of the chord sectioned between such chord and such arc equals to or longer than five-eighths of the diameter of a virtual circle composed by such arc, the instrument can have a section whose area and sectional secondary moment are larger than those of K-file, a conventional instrument for root canal therapy pierced into the content of the root canal in the first stage of the therapy. Thus the instrument can obtain bending strength and bending rigidity significantly higher than those of the K-file.

Composing the sectional form with an arc and chord can facilitate the migration of the content within the root canal.

In particular, the edges formed at the joint portions of the chord and arc can function as a cutting edge. Thus for the case that a part of the calcified root canal wall is present in a form of projection, rotating such piercing instrument can successfully resect the projection. Despite a round section is generally preferred for the piercing instrument in terms of bending strength, the present invention employs a sectional form surrounded by a chord and an arc considering the function of such cutting edge.

Another piercing instrument according to the present invention has a shaft portion and an operational portion extended from such shaft portion, wherein at least a region from the tip of the operational portion down to a predetermined distant position has a sectional form surrounded by an arc and two or three chords, a cross section thereof forming a D-shape, a length of the shortest line segment along a vertical bisector of the chord sectioned between such chord and such arc or between two chords equals to or longer than five-eighths of the diameter of a circle composed by such arc, and a length of the arc equals to or longer than a half of the circumference of a virtual circle composed by such arc.

According to such piercing instrument, cutting ability can slightly be increased as compared with the above-described piercing instrument without ruining the bending strength, while retaining a good operability in the piercing by virtue of the arc having a length equals to or longer than a half of the circumference of a virtual circle composed by such arc.

The present invention also provides a method for fabricating a dental instrument for root canal therapy having a shaft portion and an operational portion extended from such shaft portion, and at least a region from the tip of the operational portion down to a predetermined distant position has a sectional form surrounded by an arc and a chord, comprising a step for producing a tapered cylinder within a region at least from the tip of the operational portion down to a predetermined distant position; and a step for removing the sidewall portion of the cylinder so as to produce a predetermined plane.

Fabricating the piercing instrument by such method can successfully provide the product with an excellent quality at a low cost.

BRIEF DESCRIPTION OF THE DRAWINGS

The above and other objects and features of the invention are apparent to those skilled in the art from the following referred embodiments thereof when considered in conjunction with the accompanied drawing, in which:

FIGS. 1A and 1B are schematic views showing a constitution of a piercing instrument;

FIGS. 3A, 3B and 3C are schematic sectional views showing another examples of the sectional forms of the piercing portion of the piercing instrument;

FIG. 4 is a table for explaining experimental results of root canal insertion tests; and FIG. 5 is a table for explaining experimental results of the bending strength.

DETAILED DESCRIPTION OF THE INVENTION

Figure 2:
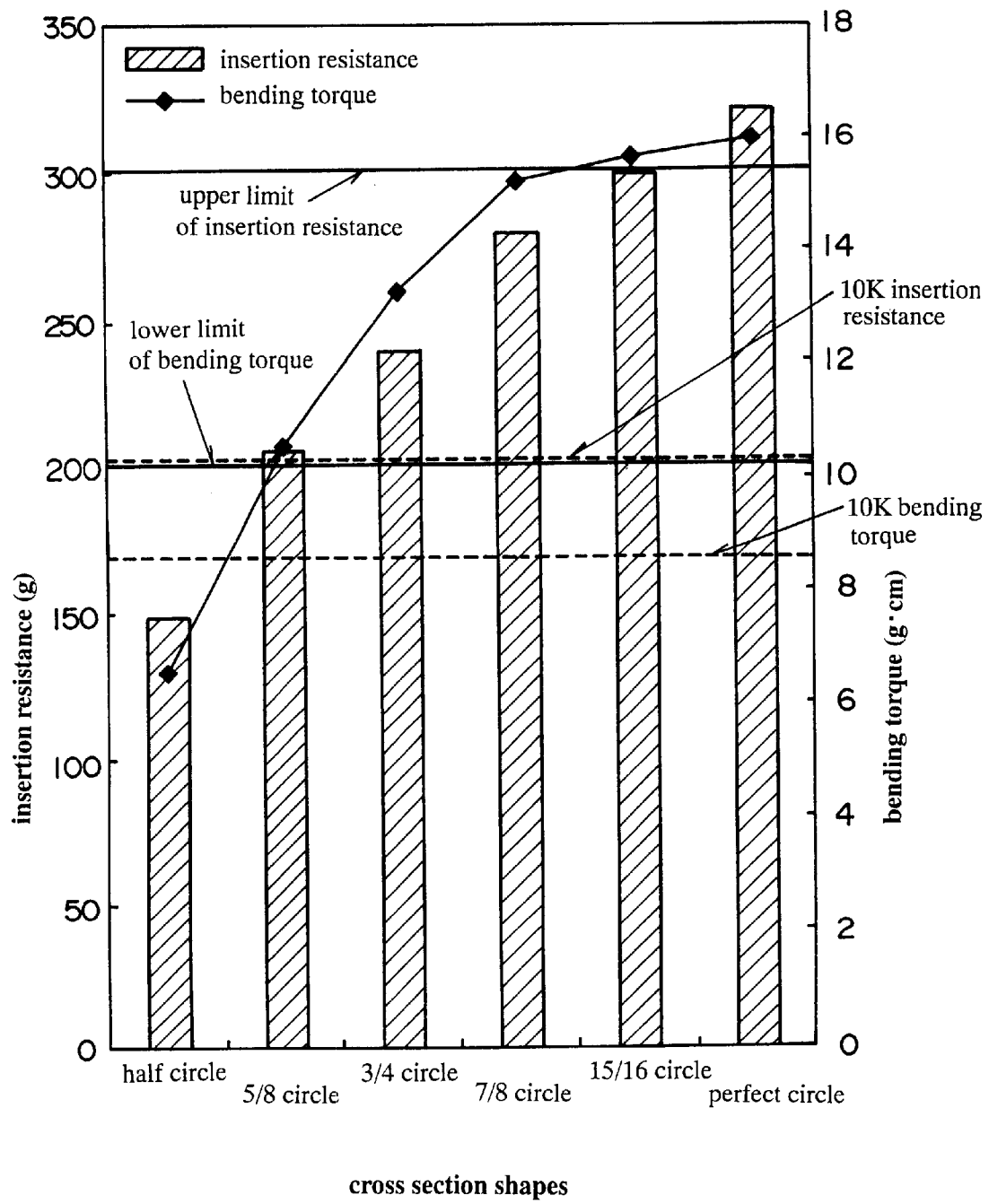
FIG. 2 is a graph explaining various experimental results in relation to set values.

Preferred embodiments of the piercing instrument will be explained hereinafter referring to the attached drawings.

As shown in FIG. 1A, a piercing instrument "A" has a shaft portion 1, an operational portion 2 extended from the shaft portion 1, and a handle 3 fixed to the shaft portion 1 to be operated while being held by a dentist's hand or attached to a hand piece.

The operational portion 2 has a piercing portion 4 within a range from the tip portion 2a down to a predetermined distant position (18 mm or less), where a sectional form of which is surrounded by an arc 4a and a chord 4b as shown in FIG. 1B, and given the diameter of a virtual circle 4g composed by the arc 4a as "D", and given the length of the line segment along a vertical bisector of the chord 4b sectioned between the arc 4a and the chord 4b as "L", the length "L" equals to or longer than ($\frac{5}{8}$)D. Such sectional form of the piercing portion 4 includes the center 4h of a virtual circle 4g. The piercing instrument "A" should be very thin since it is an instrument for creating an access route, and the diameter of the tip portion 2a of which should be within a range from 0.06 mm to 0.15 mm, more preferably 0.06 mm to 0.10 mm. Between the piercing portion 4 and the shaft 1, provided is a base portion 2b whose sectional form is not limited to as that for the piercing portion 4.

The length of the piercing portion 4 is set to 5 mm. Such length was determined based on experimental and empirical data. That is, it is a range from the tip portion to a 5 mm distant position to which an especially large force is applied during the root canal therapy, so that a length of 5 mm is sufficient for the piercing portion 4. And the piercing portion 4 has a sectional form satisfying the above-described relation of $L \geq (\frac{5}{8})D$.

A portion within the operational portion 2 other than the piercing portion 4, that is the base portion 2b, has no special limitation on its sectional form. Thus the sectional form of the base portion 2b may be such that the length "L" equals to or longer than ($\frac{5}{8}$)D, or shorter than ($\frac{5}{8}$)D. The base portion 2b is, however, preferably designed so as to have a small sectional area to reduce the bending rigidity, to thereby ensure that the bending rigidity in the longitudinal direction over the entire length of the operational portion 2b does not significantly differ from that of the piercing portion 4.

The operational portion 2 consisting of the piercing portion 4 and the base portion 2b may have a straight needle form, or may be twisted at a helix angle equivalent to that for the K-file of the same size. Creation of the access route by piercing the piercing portion 4 into the content filled in the root canal is effected by a reciprocal operation of the piercing instrument "A", where contact friction between the piercing portion 4 and the content is preferably small as possible. In this sense, the piercing portion 4 preferably has a straight needle form, where twisting with a long lead is of no special problem. Even a short lead is allowable if the piercing portion 4 is to be operated in a reciprocal motion as combined with a rotating motion. Increasing a helix angle toward the base portion 2b of the operational portion 2 may be beneficial in obtaining a good flexibility. Reducing the helix angle in a stepwise manner between the piercing portion 4, that is a portion from the tip down to the 5 mm distant position, and other portion is helpful in preventing excessive bite during the rotational operation.

A ratio of reduction in the diameter (taper angle) of the piercing portion 4 is set at a value approximately similar to that of a K-file of the same size. It is, however, also possible to increase the bending strength in the vicinity of the tip portion 2a by reducing the taper in the piercing portion 4 than in the K-file.

In this example, the operational portion 2 is made of a material having a size and a helix angle, both being approximately same with those of a K-file of the same size.

The sectional form of the piercing portion 4 was determined based on data obtained from experiments assuming the load ascribable to the resistance upon piercing the content of the root canal with the instrument (comparative tests on insertion resistance in root canal), and from experiments for measuring the bending strength of the operational portion 2 (comparative tests on bending).

In the comparative tests on insertion resistance in the root canal, a root filling point made of an isoprene-base rubber is filled in a straight root canal model (#15, $\frac{2}{100}$ taper) up to a level of 8 mm, and the resistances sensible when test pieces contact with the filled. material and go into a 3 mm depth were measured and compared. The test pieces employed are those individually having a sectional area in which the length of the line segment sectioned between the chord and the arc varies within a range from ($\frac{1}{2}$)D to ($\frac{15}{16}$)D; those having a round section; and K-file #10.

In FIGS. 4 and 5, the notation "$\frac{5}{8}$ circle" means that the length "L" of the line segment sectioned between the chord 4b and the arc 4a is set to ($\frac{5}{8}$)D. The same will apply to the other test pieces.

It was also defined from the questionnaire or other researches targeted at dentists that an upper limit of the insertion resistance during the piercing into the content of the root canal is set at 150% of the resistance sensible with the comparative K-file #10. The decision is supported by opinion of a number of clinical dentists that a magnitude of the resistance sensible during actual therapy is felt when the instrument collides on a portion constricted due to calcification or curved profile rather than during the piercing of the content, so that setting the resistance of piercing of the content at 150% is still not excessive. The set value, as the upper limit of the insertion resistance, was expressed with a solid line in FIG. 2.

Data obtained from the comparative tests on the root canal insertion were listed in FIG. 4 and expressed by a bar graph in FIG. 2.

It was found that the insertion resistance of the K-file #10 was 204.1 g (shown by a dot line with an indication of "10K insertion resistance" in FIG. 2), and the set upper limit of the resistance was 306.15 g. The value was satisfied by all instruments except for the round-sectioned instrument for the comparative purpose. It is to be noted that also a K-file #10 hardened as described in the Background Art of course showed the same insertion resistance with that of the K-file shown in FIG. 2.

In the comparative tests on bending, bending torque at a portion 3 mm distant from the tip (tip portion of the piercing portion 4) of the test pieces was measured and compared according to the procedures of the relevant ISO standard. The test pieces employed were such that having the same section with that of those employed in the comparative tests on the root canal insertion.

Since the bending torque is preferably large enough, a lower limit is set to 120% of a bending torque of the comparative K-file #10. Such setting of the bending torque at 120% is based on the opinion of a number of dentists that the bending strength larger by approx. 20% than that of the conventional K-file will be enough for piercing the content of the root canal and for creating the access route. The set value, as the lower limit of the bending torque, was expressed with a solid line in FIG. 2.

Data obtained from the comparative tests on the bending strength were listed in FIG. 5 and expressed by a kinked line graph in FIG. 2.

It was found that the bending torque of the K-file #10 was 8.7 g·cm (shown by a dot line with an indication of "10K bending torque" in FIG. 2), and the set lower limit of the bending torque was 10.4 g·cm. The value was satisfied by all instruments except for the semicircle-sectioned instrument. It is to be noted that a K-file #10 hardened showed a bending torque of 12.7 g·cm, which corresponds to the case of L=($\frac{3}{4}$)D.

It was found from these experiments that, as for the sectional form clearing the individual set limits for the tests on insertion resistance in root canal and comparative tests on bending, the length "L" of the line segment sectioned between the chord 4b and the arc 4a fell within a range from ($\frac{5}{8}$)D to ($\frac{15}{16}$)D. It was also found that even when the length "L" is longer than ($\frac{15}{16}$)D, a sectional form can clear the above limits if it is composed of a chord 4b and an arc 4a.

Thus it is concluded that the preferable sectional form of the piercing portion 4 is composed of an arc 4c and a chord 4b (excluding circle), and the length "L" of the line segment sectioned between the chord 4b and the arc 4a equals to or longer than ($\frac{5}{8}$)D.

Next, other examples of the sectional form of the piercing portion 4 of the piercing instrument "A" will be described referring to FIGS. 3A, 3B and 3C. The sectional forms of these examples shown in the figures are individually composed of an arc and two or three chords, contains the center of a virtual circle which is assumed as having no chord, and have a length of the arc equals to or longer than a half of the circumference of a virtual circle composed by such arc.

FIG. 3A shows a sectional form having a chord 4c which initiates from one end of the chord 4b; FIG. 3B shows a sectional form having chords 4c, 4d which initiate from both ends of the chord 4b, respectively; and FIG. 3C shows a sectional form having a chord 4e (corresponding to a plane generated after $\frac{3}{16}$ removal) and a chord 4f (corresponding to a plane generated after $\frac{1}{16}$ removal) arranged in parallel at the top and bottom. The piercing instruments "A" individually having such sectional forms were fabricated to provide test pieces, and bending torque at a portion 3 mm distant from the tip (tip portion of the piercing portion 4) of the test pieces was measured. The test piece corresponding to FIG. 3A was found to have a bending torque of 13.08 g·cm, the test piece corresponding to FIG. 3B of 12.9 g·cm, and the test piece corresponding to FIG. 3C of 13.5 g·cm. It was thus made clear that the case with the length "L" of ($\frac{5}{8}$)D or longer and the length of the arc 4a of semicircle or longer were not causative of significant lowering of the bending strength, and instead could improve the cutting ability. This in particular gave a good result when the calcified root canal was pierced.

A desirable level of the bending strength can be ensured when a length of the shortest line segment along a vertical bisector of the chord sectioned between such chord and such arc or between two chords equals to or longer than five-eighths of a diameter of a circle. A desirable level of the strength can be obtained since the arc is ensured to have a length equals to or longer than a half of the circumference of a virtual circle composed by such arc, and thus an angle of the edge becomes 90° or larger.

Ensuring a length of the arc equals to or longer than a half of the circumference of the circle will make the surface of the instrument less irregular, which reduces resistance upon the piercing with the instrument and allows smooth piercing.

Next, procedures for fabricating the piercing instrument "A" will be briefed hereinafter. First, a material made of austenitic stainless steel is stretched by cold wire drawing into a fiber form, cut into a length desired for a target piercing instrument "A", ground over the entire length thereof to produce a work in a tapered conical form, removed in an outer portion of the work to produce a predetermined plane (a plane corresponding to the chord 4b) by grinding or other means, to thereby obtain a sectional form of the piercing portion 4 selected from those described in the foregoing examples, as well as obtaining a sectional form of the base portion 2b. For the case that the piercing portion 4 is made in a form of a straight needle, the work as an intermediate product can be provided with a handle 3 by insert forming to thereby produce the piercing instrument "A".

In the present invention, there is no specific limitation on means and methods of the grinding to produce the piercing portion 4 of the piercing instrument "A", and any of those is allowable so long as the chords 4a, 4b (4c to 4f) can be formed in a final product.

Possible processing methods for producing the tapered conical work include cutting, grinding, rolling and swaging, where process hardening can be expected from rolling and swaging. The cutting can be effected by centerless grinding or other methods. The grinding direction may arbitrarily be selected, that is, the direction may be approximately normal to the longitudinal direction of the fiber-like material, may be at an angle other than normal, or may be the same with the longitudinal direction. It is also allowable, as in the conventional grinding method disclosed in Examined Japanese Patent Publication 58-52782, to place the fiber-like material in a groove (U-groove or V-groove) and grind under rotation the material using a grindstone.

The plane corresponding to the chord 4d can be obtained by cutting or grinding. In the grinding, the conical work can be ground while being held between a grind stone and a jig having a plane ground under pressing onto the outer periphery of such grindstone. The grinding direction may arbitrarily be selected, that is, the direction may be approximately normal to the longitudinal direction of the fiber-like material, may be at an angle other than normal, or may be the same with the longitudinal direction. It is also allowable, as in the conventional grinding method disclosed in Examined Japanese Patent Publication 58-52782, to place the fiber-like material in a groove (U-groove or V-groove) and grind under rotation the material using a grindstone.

When the piercing portion 4 twisted at a preset helix angle is formed, twisting is conducted while holding the piercing portion 4 at the arc 4a and the chord 4b using a vice. It is now to be noted that the arc 4a composing the sectional form of the piercing portion 4 may not be referred to as an arc in a precise meaning, and similarly the chord 4b may not be referred to as a chord in a precise meaning, since the piercing portion 4 is held at the arc 4a and the chord 4b with a vice.

Such problem, however, inevitably associates with the twisting, and it is to be defined that also the arc and the chord with such deformation occurred during the fabrication process can be categorized as the arc 4a and the chord 4b. Similarly, it is to be defined that the sectional form of the piercing portion 4 is composed of the arc 4a and the chord 4b irrespective of collapse or other deformation which may occur in the portion other than that held by the vice during the twist processing. The same will apply to other cases with the sectional forms shown in FIG. 3A, 3B and 3C.

In particular for the case that a plurality of the chords 4b and 4c are formed as jointed at the ends, a joint point of the arcs 4b, 4c may inwardly shift from a point on the circumference, so that the arcs 4b, 4c may not be referred to as a chord in a precise meaning. Such problem, however, almost inevitably associates with the process, and it is to be defined that also the chords with such shifting can be categorized as an arc. Even an outwardly kinked chord which can be assumed as two lines, or slightly bowed chord which can be assumed as a curve, may also be referred to as chords provided that they can substantially exhibit similar effect expected in the present invention.

While the foregoing example employed austenitic stainless steel as a material, the material may be a nickel-titanium alloy having a shape memory effect. In such case, proper selection of processing and annealing conditions will be helpful in processing the shaft portion 1 and the operational portion 2 in a superelastic region.

It is preferable to mirror-finish the surface along the arc 4a to reduce the resistance during the piercing. For the case that a plurality of joint points are formed between the arc 4a and the chords 4b to 4f, or between the chords 4b and 4c, it is also preferable to round a selected number of the joint point(s). In this case, the residual joint point(s) can function as a cutting edge while the rounded joint point(s) does not.

The handle 3 connected to the shaft portion 1 is not always necessary, and the shaft portion 1, intended for use as attached to devices such as a hand piece or engine, may be composed so as to be chucked with a corresponding device.

It is preferable to vary a value of "L" and taper ratio in the piercing portion 4, so as to upgrade uniformity in the bending strength or bending rigidity over the entire length of such piercing portion 4. Ratios of these parameters are not strictly limited and may properly be selected depending on the diameter or taper angle of the piercing instrument "A". While general files are manufactured at a taper ratio of 2/100, the instrument of the present invention may be manufactured at a taper ratio equals to, larger than, or smaller than 2/100.

While the instrument of the present invention has been described as being typified by a piercing instrument, the instrument of the present invention is beneficial also when used for mechanical cutting mainly operated with a rotating or twisting motion. Conventional root canal reamer tends to bite deeply into the root canal wall due to its excessive sharpness, which has been overcome with various countermeasures. On the other hand, the instrument of the present invention has a dull edge (at an angle of 90° or more) and has a less number of cutting edge(s), so that it is favorable enough that the bite is unlikely to occur. For the case that the instrument of the present invention is used for mechanical cutting, it is preferable to use the instrument having a tip diameter as somewhat large as 0.15 mm or above, since larger diameter increases the area of the plane along the circumference and can stabilize the cutting.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention shall not be limited by the specification, but shall be defined by the claims set forth below.

What is claimed is:

1. A dental instrument for root canal therapy comprising:
    a shaft portion; and
    an operational portion extended from such shaft portion having a single spiral groove, a cross section thereof forming a D-shape,
    wherein at least a region from the tip of the operational portion down to a predetermined distant position has a sectional form surrounded by an arc and a chord, and a length of a line segment along a vertical bisector of the chord sectioned between such chord and such arc equals to or is longer than five-eighths of the diameter of a virtual circle composed by such arc.

2. A dental instrument for root canal therapy comprising:
    a shaft portion; and
    an operational portion extended from such shaft portion having a single spiral groove, a cross section thereof forming a D-shape, wherein at least a region from the tip of the operational portion down to a predetermined distant position has a sectional form surrounded by an arc and two or three chords, a length of the shortest line segment along a vertical bisector of the chord sectioned between such chord and such arc or between two chord equals to or longer than five-eighths of the diameter of a circle composed by such arc, and a length of the arc equals to or is longer than a half of the circumference of a virtual circle composed by such arc.

3. A method for fabricating a dental instrument for root canal therapy having a shaft portion and an operational portion extended from such shaft portion having a single spiral groove, and at least a region from the tip of the operational portion down to a predetermined distant position has a sectional form surrounded by an arc having a surface and a chord, comprising:

a first step comprising producing a tapered cylinder within a region at least from the tip of the operational portion down to a predetermined distant position;

a second step comprising removing the sidewall portion of the cylinder so as to produce a predetermined plane;

a third step comprising spirally twisting the operational portion while maintaining the plane; and a fourth step comprising mirror-finishing the surface of the arc.

4. A dental instrument for root canal as claimed in claim 1, wherein the instrument is made of austenitic stainless steel drawn into a fiber form.

5. A dental instrument for root canal as claimed in claims 1,2,4 and 5, wherein the operational portion has a virtual diameter of 18 mm or less, and the tip of such operational portion has a virtual diameter of 0.06 to 0.15 mm.

6. A dental instrument for root canal as claimed in claim 2, wherein the instrument is made of austenitic stainless steel drawn into a fiber form.

7. A dental instrument for root canal as claimed in claim 2, wherein the operational portion has a virtual diameter of 18 mm or less, and the tip of such operational portion has a virtual diameter of 0.06 to 0.15 mm.

* * * * *